US00PP31546P2

(12) United States Plant Patent
van Sambeek

(10) Patent No.: US PP31,546 P2
(45) Date of Patent: Mar. 10, 2020

(54) ***SALVIA* PLANT NAMED 'DOSASKIMI'**

(50) Latin Name: *Salvia nemorosa*
Varietal Denomination: Dosaskimi

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/350,645

(22) Filed: Dec. 14, 2018

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Salvia* plant named 'Dosaskimi', characterized by its compact and upright plant habit; vigorous growth habit; freely branching habit; early and freely flowering habit; upright inflorescences with violet blue-colored flowers; and good garden performance.

1 Drawing Sheet

Botanical designation: *Salvia nemorosa.*
Cultivar denomination: 'DOSASKIMI'.

BACKGROUND OF THE INVENTION

The present invention relates to a new and distinct cultivar of *Salvia* plant, botanically known as *Salvia nemorosa* and hereinafter referred to by the name 'Dosaskimi'.

The new *Salvia* plant is a product of a planned breeding program conducted by the Inventor in Aalsmeer, The Netherlands. The objective of the breeding program is to create new compact *Salvia* plants with numerous attractive flowers.

The new *Salvia* plant originated from a cross-pollination in June, 2013 of a proprietary selection of *Salvia nemorosa* identified as code number SV-0007, not patented, as the female, or seed, parent with a proprietary selection of *Salvia nemorosa* identified as code number SV-0017, not patented, as the male, or pollen, parent. The new *Salvia* plant was discovered and selected by the Inventor as a single flowering plant from within the progeny of the stated cross-pollination in a controlled environment in Aalsmeer, The Netherlands in June, 2014.

Asexual reproduction of the new cultivar by vegetative terminal cuttings in Aalsmeer, The Netherlands, since July, 2014 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dosaskimi'. These characteristics in combination distinguish 'Dosaskimi' as a new and distinct *Salvia* plant:

1. Compact and upright plant habit.
2. Vigorous growth habit.
3. Freely branching habit.
4. Early and freely flowering habit.
5. Upright inflorescences with violet blue-colored flowers.
6. Good garden performance.

Plants of the new *Salvia* can be compared to plants of the female parent selection. Plants of the new *Salvia* differ primarily from plants of the female parent selection in the following characteristics:

1. Plants of the new *Salvia* are more compact than plants of the female parent selection.
2. Plants of the new *Salvia* are more upright than and not as outwardly spreading as plants of the female parent selection.

Plants of the new *Salvia* can be compared to plants of the male parent selection. Plants of the new *Salvia* differ primarily from plants of the male parent selection in the following characteristics:

1. Plants of the new *Salvia* are more compact than plants of the male parent selection.
2. Plants of the new *Salvia* and the male parent selection differ in flower color as plants of the new *Salvia* have violet blue-colored flowers whereas plants of the male parent selection have pink-colored flowers.

Plants of the new *Salvia* can be compared to plants of *Salvia nemorosa* 'May Night', not patented. In side-by-side comparisons, plants of the new *Salvia* differ from plants of 'May Night' in the following characteristics:

1. Plants of the new *Salvia* are more compact than plants of 'May Night'.
2. Plants of the new *Salvia* are more upright than and not as outwardly spreading as plants of 'May Night'.
3. Plants of the new *Salvia* are more freely branching than plants of 'May Night'.

4. Plants of the new *Salvia* have smaller and darker green-colored leaves than plants of 'May Night'.
5. Plants of the new *Salvia* have shorter inflorescences than plants of 'May Night'.
6. Plants of the new *Salvia* are more freely flowering than plants of 'May Night'.
7. Plants of the new *Salvia* have smaller flowers than plants of 'May Night'.
8. Plants of the new *Salvia* have shorter peduncles than plants of 'May Night'.

BRIEF DESCRIPTION OF THE PHOTOGRAPH

The accompanying colored photograph illustrates the overall appearance of the new *Salvia* plant showing the colors as true as it is reasonably possible to obtain in colored reproductions of this type. Colors in the photograph may differ slightly from the color values cited in the detailed botanical description which accurately describe the actual colors of the new *Salvia* plant. The photograph is a side perspective view of a typical flowering plant of 'Dosaskimi' grown in a container.

DETAILED BOTANICAL DESCRIPTION

The aforementioned photograph and following observations, measurements and values describe plants grown during the spring and early summer in 13-cm containers in an outdoor nursery in Aalsmeer, The Netherlands and under cultural practices typical of commercial *Salvia* production. During the production of the plants, day temperatures averaged 20° C. and night temperatures averaged 16° C. Plants were pinched one time and were three months old when the photograph was taken and 14 weeks old when the description was taken. In the detailed description, color references are made to The Royal Horticultural Society Colour Chart, 2007 Edition, except where general terms of ordinary dictionary significance are used.

Botanical classification: *Salvia nemorosa* 'Dosaskimi'.

Parentage:

*Female, or seed, parent.*—Proprietary selection of *Salvia nemorosa* identified as code number SV-0007, not patented.

*Male, or pollen, parent.*—Proprietary selection of *Salvia nemorosa* identified as code number SV-0017, not patented.

Propagation:

*Type.*—By vegetative terminal cuttings.

*Time to initiate roots, summer.*—About ten days at temperatures about 26° C.

*Time to initiate roots, winter.*—About two weeks at temperatures about 23° C.

*Time to produce a rooted young plant, summer.*—About twelve days at temperatures about 23° C.

*Time to produce a rooted young plant, winter.*—About 16 days at temperatures about 18° C.

*Root description.*—Medium in thickness, fibrous; typically white to light yellow in color, actual color of the roots is dependent on substrate composition, water quality, fertilizer type and formulation, substrate temperature and physiological age of roots.

*Rooting habit.*—Moderately freely branching; dense.

Plant description:

*Plant and growth habit.*—Herbaceous perennial typically grown as a container and garden plant; upright plant habit; uniform and vigorous growth habit; rapid growth rate.

*Branching habit.*—Freely basal branching with about eight primary lateral branches developing per plant.

*Plant height.*—Compact, about 20 cm.

*Plant width.*—About 15 cm.

*Lateral branch description.*—Length: About 20 cm. Internode length: About 4 cm. Strength: Strong. Aspect: Mostly upright. Texture: Pubescent. Color: Close to 138B; random spots, close to 187A.

Leaf description:

*Arrangement.*—Opposite, simple.

*Length.*—About 6 cm.

*Width.*—About 2.5 cm.

*Shape.*—Elliptical.

*Apex.*—Acute.

*Base.*—Cordate.

*Margin.*—Crenate, fine pubescence along edge.

*Texture, upper surface.*—Rugose, glabrous.

*Texture, lower surface.*—Pubescent.

*Venation pattern.*—Pinnate, reticulate.

*Color.*—Developing leaves, upper surface: Close to 139A. Developing leaves, lower surface: Close to 137B. Fully expanded leaves, upper surface: Close to 139A; venation, close to 148C. Fully expanded leaves, lower surface: Close to 137C; venation, close to 148C.

*Petioles.*—Length: About 2.5 cm. Diameter: About 2 mm. Texture, upper and lower surfaces: Pubescent. Color, upper surface: Close to 139C. Color, lower surface: Close to 138C.

Flower description:

*Flower arrangement and shape.*—Single bilabiate flowers arranged on erect spikes; freely flowering habit with about 60 flowers developing per inflorescence and about 1,400 flowers developing per plant during the flowering season; flowers face mostly outwardly.

*Fragrance.*—None detected.

*Natural flowering season.*—Early flowering habit, plants begin flowering about six weeks after planting; plants flower during June and July in an outdoor environment in The Netherlands; flowers not persistent.

*Flower buds.*—Length: About 4 mm to 5 mm. Diameter: About 2 mm. Shape: Conical. Color: Close to 93A.

*Inflorescence height.*—About 6.5 cm.

*Inflorescence diameter.*—About 2 cm.

*Flower diameter.*—About 4 mm.

*Flower height.*—About 1 cm.

*Flower throat diameter.*—About 2 mm.

*Flower tube length.*—About 5 mm.

*Flower tube diameter, proximally.*—About 2 mm.

*Petals.*—Arrangement: Five petals fused at the base; one upper banner petal (upper lip), two lateral petals and two lower petals (lower lip). Lobe length: About 5 mm. Lobe width: About 1 mm. Shape: Round. Apex: Round. Base: Fused into a narrow tube. Margin: Entire. Texture, upper surface: Smooth, glabrous. Texture, lower surface: Pubescent. Texture, throat: Smooth, glabrous. Texture, tube: Smooth, glabrous. Color: When opening, upper and lower surfaces: Close to 93B. Fully opened, upper and lower surfaces: Close to 93B; venation, close to 93B; color does not change with development. Throat: Close to 92D; venation, close to 92D. Tube: Close to 92D; venation, close to 92D.

*Calyx.*—Arrangement: Five sepals fused to form a campanulate calyx. Length: About 5 mm. Width: About 2 mm. Shape: Deltoid. Apex: Acuminate. Margin: Entire; ciliate. Texture, inner and outer surfaces: Smooth, glabrous. Color, inner surface: Close to 79A. Color, outer surface: Close to 146D.

*Peduncles.*—Length: About 13 cm. Diameter: About 2 mm. Strength: Strong. Aspect: About 20° from vertical. Texture: Pubescent. Color: Close to 138B; random sectors and spots, close to 187A.

*Pedicels.*—Length: About 2 mm. Diameter: About 0.5 mm. Strength: Flexible. Aspect: About 20° from vertical. Texture: Pubescent. Color: Close to 59B.

*Reproductive organs.*—Stamens: Quantity per flower: Two. Filament length: About 2 mm. Filament color: Close to 92A. Anther shape: Oblique. Anther length: About 0.5 mm. Anther color: Close to 164B. Pollen amount: None observed. Pistils: Quantity per flower: One. Pistil length: About 1 cm. Stigma shape: Biparted. Stigma color: Close to 93A. Style length: About 8 mm. Style color: Close to 92A. Ovary color: Close to 145B.

*Seeds and fruits.*—To date, seed and fruit production has not been observed on plants of the new *Salvia.*

Pathogen & pest resistance: To date, plants of the new *Salvia* have not been noted to be resistant to pathogens and pests common to *Salvia* plants.

Garden performance: Plants of the new *Salvia* have exhibited good garden performance and to be tolerant to rain, wind and temperatures ranging from about −20° C. to about 30° C.

It is claimed:

1. A new and distinct *Salvia* plant named 'Dosaskimi' as illustrated and described.

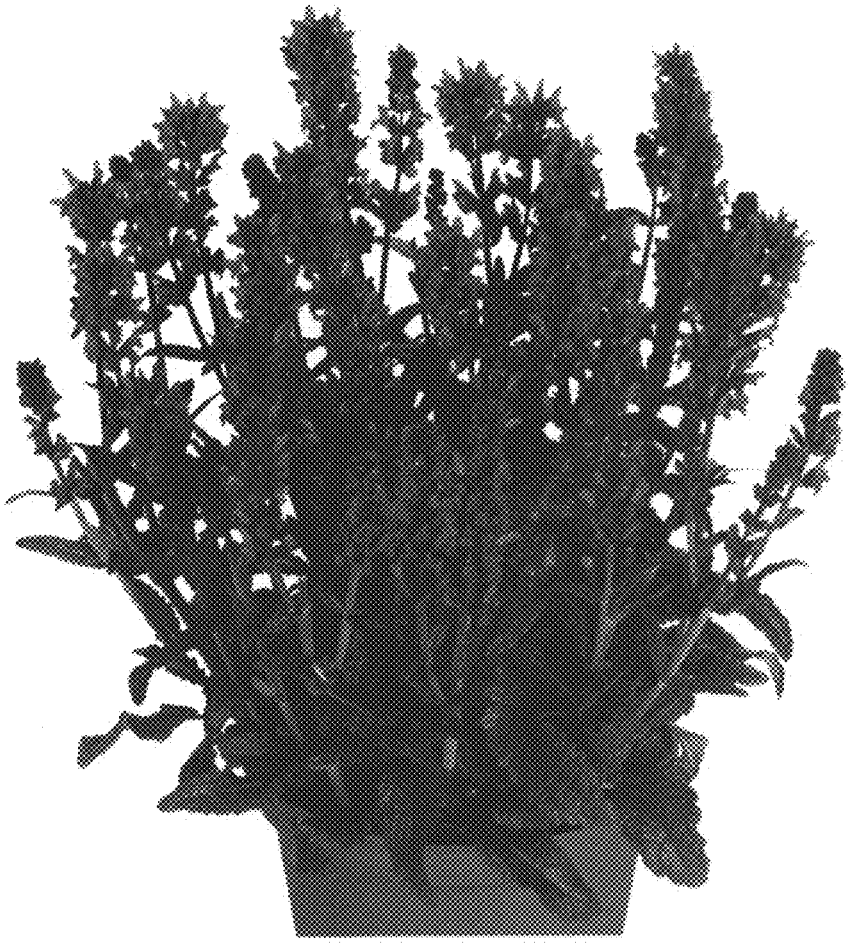

* * * * *